United States Patent [19]
Kleinmann

[11] Patent Number: 5,653,589
[45] Date of Patent: Aug. 5, 1997

[54] COLOR KEY

[75] Inventor: Jurg Kleinmann, Triesen, Liechtenstein

[73] Assignee: Ivoclar AG, Liechtenstein

[21] Appl. No.: 616,665

[22] Filed: Mar. 15, 1996

[30]  Foreign Application Priority Data

Mar. 17, 1995 [DE] Germany ............... 195 09 830.7

[51] Int. Cl.⁶ ................................................ A61C 19/10
[52] U.S. Cl. ...................................... 433/26; 206/83
[58] Field of Search ................ 433/26, 229; 206/63.5, 206/83, 368, 369

[56]  References Cited

U.S. PATENT DOCUMENTS 537,553   4/1895   Starr ........................................ 206/83
5,149,267  9/1992  Longhini et al. ......................... 433/26
5,261,815  11/1993 Pozzi ......................................... 433/26

*Primary Examiner*—Nicholas D. Lucchesi
*Attorney, Agent, or Firm*—Alan S. Korman; John C. Thompson

[57]  ABSTRACT

A color key (10) useful as an aid for the selection of the color of artificial teeth. The color key receives a plurality of color sticks (14), each stick having a colored area at one end which corresponds in color to an artificial tooth. The color key includes a plurality of individual insertion pockets (12), each of which pockets has a stick receiving unit (22) which may receive an individual color stick, and which insertion pockets (12) may be attached to one another individually substantially laterally to the extent of the stick receiving unit (22). By using this construction the color key can be quite individually adapted to the needs of the practice of the dentist or dental technician.

15 Claims, 1 Drawing Sheet

COLOR KEY

The invention relates to a color key, in particular as an aid for the selection of the color of artificial teeth wherein the color key is formed of a plurality of insertion pockets which may be releasably attached to one another individually. The term artificial teeth is taken to mean fillings, inlays/onlays, crowns and bridges, teeth themselves, as well as the materials for the production of restorations.

BACKGROUND OF THE INVENTION

Such a color key, as it became known, for example, from the German utility patent DE-GM 83 29 441, exhibits a body with several insertion pockets, into which color selection sticks may be inserted. The color selection sticks may, in keeping with the desires of the dental technician or the dentist, be assembled in random fashion, since the individual insertion pockets are embodied in an identical manner and no coding of the color selection sticks is undertaken to assure reception in only one particular insertion pocket or color selection pocket.

In keeping with the varied coloration of natural teeth, the necessity to offer a plurality of possible colors exists. A color selection from among, for example, 20 different colors, is practically a minimum to satisfy the needs of the patient to that extent. Now, if the individual color selection sticks are removed and held next to the natural teeth, so as to render a comparison possible in this way, the danger exists that they will not be replaced in their original color selection pocket, but rather, to another empty spot. Therefore, in the case of a color key according to DE-GM 83 29 441, a chaotic situation will arise sooner or later, due to the color sticks that are replaced together all at once.

Furthermore, as a matter of principle, it would be desirable to approach the patient with a certain preliminary selection of possible colors for the selection. For example, in many cases, there is a tendency toward the rather darker shades, toward more reddish shades, or toward lighter shades, so that the other colors are eliminated a priori.

Therefore, it has already been known how to embody the color key in modular fashion, as is provided in the case, for example, of the "Chromascop—Universalfarbschlüssel" [Chromascope Universal Color Key] made by the firm of Ivoclar AG. In this process, 4 similar colors that are assembled in a common carrier that is coded according to a basic color, are stored, summarized on the color key. To this end, the color key exhibits corresponding recesses for the interchangeable reception of a plurality of carriers, so that there already exists a certain freedom of arrangement.

Furthermore, it has even been suggested that several color keys be coupled to one another in order to facilitate dealing with larger dolor keys. This solution, however, entails a rather complex creation of color keys of this type, even though, basically, the disadvantages of the color key according to the aforementioned utility patent are not eliminated.

Basically, various possibilities exist for the classification of mixed colors. One possibility resides in using lightness as a basis, and summarizing one color group each, thus, colors having an emphasis in a particular underlying color, by means of similar combinations of numbers or letters. Mixed colors between various groups of colors, can then be designated by intervening combinations of numbers or letters.

The precise designation of the colors is very important, since only by means of definite identification is it assured that the dental technician uses the right teeth. Faulty designations can give rise to the production of faulty dentures that can no longer be used.

Currently, there are, among others, the Kerascop color designation key, and the Chromascop designation key. Assignment of the most important of these colors to both color designation keys may be accomplished by means of the following table:

| | | | | | | |
|---|---|---|---|---|---|---|
| 110 | 01 | | | | | |
| 120 | | 1A | | | | |
| 130 | | | 2A | | | |
| 140 | | 1C | | | | |
| 210 | | | 2B | | | |
| 220 | | 1D | | | | |
| 230 | | 1E | | | | |
| 240 | | | 2C | | | |
| 310 | | | | 3A | | |
| 320 | | | | | 5B | |
| 330 | | | 2E | | | |
| 340 | | | | 3E | | |
| 410 | | | | 4A | | |
| 420 | | | | | | 6B |
| 430 | | | | | 4B | |
| 440 | | | | | | 6C |
| 510 | | | | | | 6D |
| 520 | | | | | 4C | |
| 530 | | | | 3C | | |
| 540 | | | | | 4D | |

From this overview, it becomes apparent that on the basis of the various points of view according to which tooth colors may be classified, a purely linear arrangement of colors does not, by its nature, do justice to the differences. The structure of color categorization that is afforded by the known color keys is therefore, basically, too rigid to be able to be used for all conceivable schemes of classification, and to that extent, it represents a compromise.

OBJECTS AND SUMMARY OF THE INVENTION

By contrast, it is the underlying task of the invention to create a color key which may be individually adjusted to meet the needs of the particular dentist or dental technician.

This task is met by a color key useful as an aid for the selection of the color of artificial teeth, the color key being capable of receiving a plurality of color sticks, each stick having a colored area at one end which corresponds in color to an artificial tooth. The color key includes a plurality of individual insertion pockets, each of which pockets has a stick receiving unit which may receive an individual color stick, and which insertion pockets may be attached to one another individually substantially laterally to the extent of the stick receiving unit.

With the solution according to the invention, the color key can be quite individually adapted to the needs of the practice the particular dentist or laboratory technician. For example, the colors may be sorted either according to the Kerascop [Kerascope] or the Chromascope color designation key. If, for example, the dentist or dental technician desires a gradation of color from yellow to gray with a constant level of lightness, it is possible, even for this assembly of colors, to cause the insertion pockets to stick to one another in the desired sequence.

It is particularly favorable that as a result of the individual ability to cause adherence, the color key may be expanded at will, so that, for example, in the case of patients who enjoy the selection process to a greater degree, a greater number of colors can be offered, whereas, in the case of patients who require more counselling, the color key may be reduced in size, so as not to confuse the patient.

The color key according to the invention may be produced in a particularly cost-effective manner, due to the fact that different frames, depending upon the color designation key to be used, and the tools necessary for it need not be produced, but rather, by contrast, only an insertion pocket as the fundamental element for an arbitrary arrangement in a straight line, and, preferably, a left end and a right end piece. Surprisingly, the stability of the color key is by no means unsatisfactory, despite the individual attachability, to which end the intensive penetration of the insertion elements into one another makes a contribution. For example, an insertion pocket of the type being observed can, in virtually in its total basic surface, be penetrated by an insertion peg from an insertion pocket attached to it from the left, while it, itself, exhibits an insertion peg, which extends toward the right across nearly its entire length and width, and is provided to engage a liner of an insertion pocket that is attached to the right of it.

This embodiment permits space-saving insertion, whereby particularly good utilization is made of the fact that the stick receiving units of the color sticks and the liners for the attachment can overlap each other in the projection.

Preferably, a definite arrangement for the insertion is provided, so that the individual insertion pockets can be attached to one another in only one position. Due to the fact that the insertion pockets may be attached individually to one another, random lengths and insertion combinations of the color key can be realized. A slightly arched embodiment of both the peg and the liner lends itself well to the assurance of a definite insertion position, and, in addition, it is hand-friendly.

When using a somewhat elastic plastic for the insertion pockets, certainty of insertion is assured to a sufficient degree without requiring a highly exact fit between the insertion elements, liner and peg. It is enough to provide play-free fit, and a re-working of the surface is not necessary.

The mutual, nearly complete penetration of the insertion pockets with respect to their adjacent insertion pockets also renders it possible to spread the color key in the form of an arc, so that the colored surfaces are at a greater distance from one another than would be the case according to the grid of the insertion pockets.

In this process, as a discretionary matter, the pegs may be embodied so as to be hollow, as a result of which savings can be achieved in terms of weight and material used, or, for the sake of simplicity, they may be solid.

It will be understood that the insertion pockets can, if desired, be such that they may be written upon on their anterior side, so as to render the assignment of the color sticks to the individual insertion pockets possible, such that it is also conceivable that a neutral embodiment be selected.

Additional advantages, details, and characteristics arise from the following description of an example of an embodiment by virtue of the drawing.

DETAILED DESCRIPTION

Figure 1:
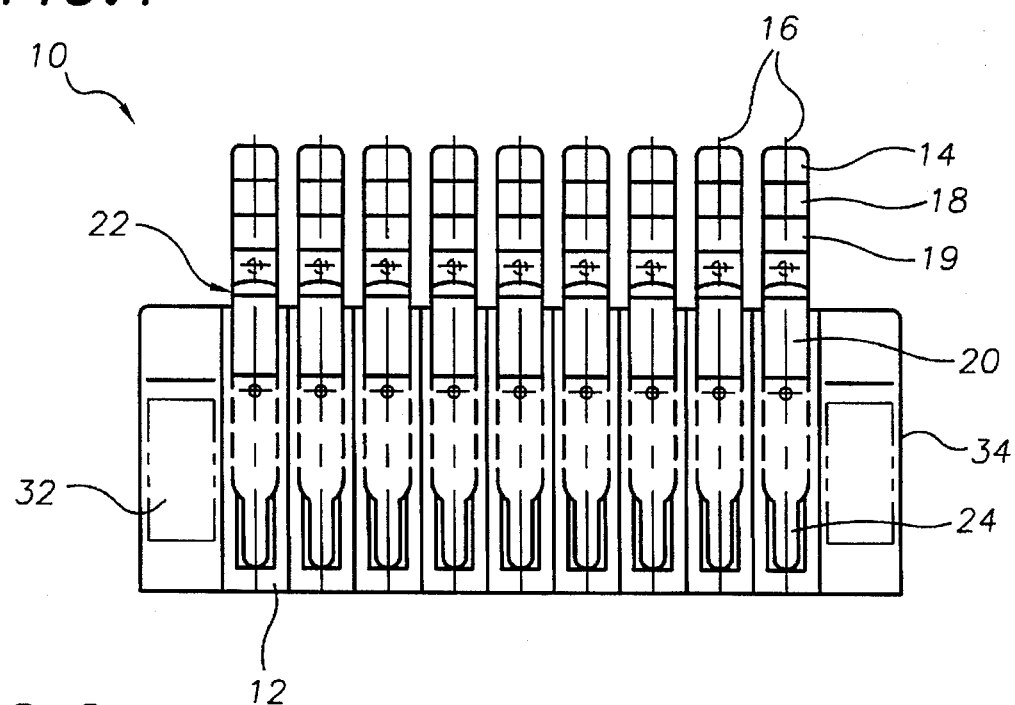
FIG. 1 shows a front view of one form of embodiment of a color key according to the invention.

The embodiment form of a color key according to the invention, 10, that is depicted in FIG. 1, consists of a plurality of insertion pockets, 12, into each of which, a color stick, 14, is inserted. In the representation according to FIG. 1, nine insertion pockets, 12, and nine color sticks, 14, are provided, such that it will be understood that another, arbitrary number of insertion pockets and color sticks may be attached to each other.

The insertion pockets, 12, exhibit, among one another, the same structure, so that the individual axis, 16, of the color sticks is arranged in a grid, and adjacent axes, 16, are each equidistant from one another. In this grid, in the compressed storage state, the insertion pockets 12 are also arranged.

Each color stick, 14, exhibits a colored surface, 18, at its upper end, and a stick, 20. Below the colored surface, 18, an area for a label, 19, is embodied, which renders a definite identification of the color stick, 14 possible. With the stick, 20, it is inserted into a stick receiving unit, 22, in the insertion pocket, 12, which is open toward the top.

The stick, 20, may be flat, or chased, for example, and it may exhibit a residual nose, in order to permit secure arresting in the insertion position. Insertion is facilitated by a narrowing, 24, which is provided at the bottom.

For the selection of the color, the dentist or dental technician removes the color stick, 14, that is under consideration, and holds it up to the patient's mouth to render a comparison of color with existing teeth possible. In this process, the selection of color should be undertaken in such a way that—in keeping with the gradation of natural teeth—not every tooth exhibits the same color, but rather, certain distributions are incorporated. Therefore, it is important to keep several color sticks ready, which make it possible to assess among one another, similar, but different shades, so that regularly, several color sticks, 14, can be removed from their insertion pockets, 12, and then replaced in the individual insertion or coupling pocket.

The insertion pockets, 12, exhibit insertion elements, 26, which are more readily visible from the additional figures, namely a liner or female element 28 and a peg or male element, 30. It will be understood that instead of the combination depicted here, that of a liner, 28, and a peg, 30, other arbitrary suitable coupling elements, 26, may be used, including, for example, an insertion unit-liner combination that is embodied in such a way as to preclude erroneous placement.

The color key, 10, exhibits, in the case of the embodiment example according to FIG. 1, a right and left end piece, 32 and 34. The end pieces, 32 and 34, are each equipped with a corresponding liner, 28 and a peg, 30, but they exhibit no stick receiving unit, 22.

Figure 2:
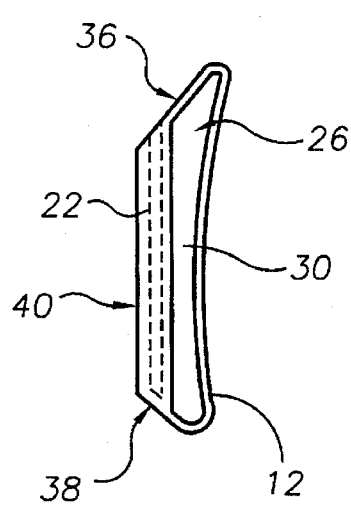
FIG. 2 shows a lateral view of an insertion pocket for the color key according to FIG. 1.

From FIG. 2, it may be seen that the peg, 30, in its length, extends nearly across the total length of the insertion pocket, 12. At its lower end, on the right, as depicted in FIG. 2, it is curved, in keeping with the course of the arc-shaped curvature of the insertion pocket 12 at its lower end. The peg, 30, as well as the insertion pocket, 12, exhibits, in profile, a certain asymmetry, which permits only one definite insertion position. The insertion pocket, 12, exhibits an upper, transverse surface, 36, and a lower transverse surface, 38, such that the upper transverse surface, 36, runs more flatly, and facilitates the introduction of the color stick 14, into the stick receiving unit, 22.

An anterior surface, 40, exhibits a comparatively large surface, and it permits, if necessary, a labelling of the insertion pocket 12.

Figure 3:
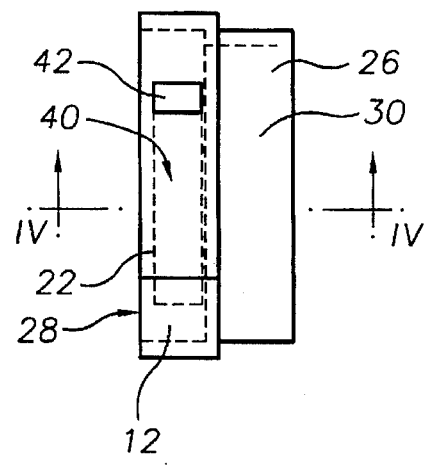
FIG. 3 shows a view from the top onto an insertion pocket according to FIG. 2.

As may be seen more readily from FIG. 3, anterior area, 40, terminates at an opening for a stick, 42. The stick receiving unit 22 extends across a considerable proportion of the insertion pocket, 12. The liner, 28, which is illustrated by broken lines, and which exhibits substantially the same dimensions as a peg 30, extends across an even greater proportion in FIG. 3. The peg, 30, has a length, width, and configuration that fits the liner 28, and, in the assembled state of the color key, 10, it disappears into the adjacent insertion pocket, 12, on the right.

Figure 4:
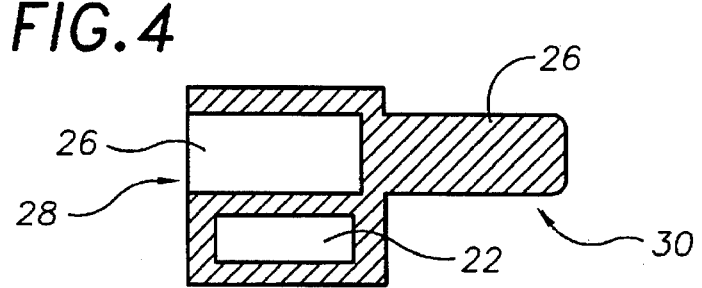
FIG. 4 shows a section through an insertion pocket along the line IV—IV from FIG. 3.

From FIG. 4, it is possible to see that liner 28 and stick receiving unit 22, can extend above one another so as to save space. In this embodiment form, the peg, 30, is solid. It may, however, also be embodied as a hollow, somewhat narrowed continuation of the liner 28, which serves to save weight.

In the embodiment example that is shown, the peg, 30, supports itself across its entire surface internally on the liner, 28. It will be understood that instead of this, support at only several points is possible as well. For example, the peg, 30, could be embodied in such a way that it exhibits at its ends, that is, adjacent to the transverse surfaces 36 and 38 the shape that is appropriate to the liner, 28, in that in the area that extends between these areas, nothing more than a thin ridge, if necessary, with support at one end, is provided.

What is claimed is:

1. A color key useful as an aid for the selection of the color of artificial teeth, the color key comprising:

a plurality of individual insertion pockets (12) which are releasably attached laterally to one another individually to form a row of insertion pockets, each insertion pocket being provided with a stick receiving unit (22) transverse to the row of insertion pockets (12); and a plurality of color sticks (14), each color stick having a colored area at one end which corresponds in color to an artificial tooth, each stick being releasably inserted into an associated stick receiving unit (22).

2. A color key according to claim 1 wherein the insertion pockets (12) are constructed in modular fashion, the insertion pockets having the same width, each insertion pocket having on one side a peg (30), and on the opposite side a liner (28) for coupling the pockets together.

3. A color key according to claim 2 wherein the peg (30) and liner (28) of each insertion pocket (12) extend over a greater length than an associated stick receiving unit (22) for the receival of the color stick.

4. A color key according to claim 3 wherein the pegs (30) that are provided as coupling elements (26) for the attachment of the insertion pockets (12) to one another completely fill the liners (28) of the insertion pockets (12), which are also provided as coupling elements (26).

5. A color key according to claim 1 wherein the insertion pockets (12) each have a peg (30) and a liner (28), whose depth of insertion is between 50% and 110% of the width of the insertion pockets (12).

6. A color key according to claim 1 wherein each insertion pocket (12) is provided with coupling elements (26) that are suitable for attachment to other insertion pockets (12), and which extend in a plane below an associated stick receiving unit (22) for the insertion of the color stick (14).

7. A color key according to claim 6 wherein the coupling elements (26) of the insertion pockets (12) are a peg (30) and a liner (28), which fit one another, and which are, curved in the form of an arc.

8. A color key according to claim 6 wherein the coupling elements (26) of each insertion pocket (12) when viewed in the direction of an associated stick receiving unit (22) for the acceptance of the color stick (14) extend across nearly the entire length of the insertion pocket (12), especially across 85 to 98% of the length of the insertion pockets.

9. A color key according to claim 6 wherein the withdrawal force of the coupling elements (26) is between about 5 and 8 N and the withdrawal force varies from one coupling element to another by not more than 50%.

10. A color key according to claim 6 wherein the coupling elements (26) have an elasticity such that the color key (10) may be spread out so that the colored areas (18) have a greater distance than the widths of the insertion pockets (12) without sacrificing the position of the insertion pockets (12) with respect to one another.

11. A color key according to claim 1 wherein the insertion pockets (12) are formed from an impact-resistant and elastic plastic.

12. A color key according to claim 1 wherein the coupling elements (26) of the insertion pockets (12) have a fit that is free of play, and that they hold to one another in an interlocking manner.

13. A color key according to claim 1 wherein the underside of each of the insertion pockets (12) is arched in a concave manner.

14. A color key useful as an aid for the selection of a color of artificial teeth, the color key comprising:

a plurality of individual insertion pockets (12) which are releasably attached laterally to one another individually to form a row of insertion pockets, each insertion pocket being provided with a stick receiving unit (22) transverse to the row of insertion pockets (12); and a plurality of color sticks (14), each color stick having a colored area at one end which corresponds in color to an artificial tooth, each stick being releasably inserted into an associated stick receiving unit (22);

the weight of the combination of an individual insertion pocket and associated color stick being between 3 and 5.5 g.

15. The color key as set forth in claim 14 wherein each insertion pocket (12) is provided with coupling elements (26) that are suitable for attachment to other insertion pockets (12), and further characterized by the fact that the coupling elements (26) of the insertion pockets (12) are held to one another with a defined retaining force, with the retaining force being greater than 5 times the weight of the combination of an insertion pocket (12) and a color stick (14).

* * * * *